United States Patent
Phung et al.

(10) Patent No.: US 6,450,951 B2
(45) Date of Patent: *Sep. 17, 2002

(54) SUTURE ORGANIZING DEVICE FOR SURGICAL RETRACTOR AND METHODS RELATED THERETO

(75) Inventors: Trinh D. Phung, Attleboro, MA (US); Thomas E. Martin, Riverside, RI (US); Matthew L. Parsons, Randolph, MA (US); Michael A. Valerio, Wrentham, MA (US)

(73) Assignee: Genzyme Corporation, Cambridge, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/491,999

(22) Filed: Jan. 26, 2000

(51) Int. Cl.[7] .................................................. A61B 1/30
(52) U.S. Cl. ...................................................... 600/215
(58) Field of Search .............................. 600/201, 204, 600/210, 214, 215; 206/63.3; 623/2; 606/148

(56) References Cited

U.S. PATENT DOCUMENTS

| | | | |
|---|---|---|---|
| 4,185,636 A | * | 1/1980 | Gabby et al. ............... 606/148 |
| 4,492,229 A | | 1/1985 | Grunwald |
| 4,627,421 A | | 12/1986 | Symbas et al. |
| 4,852,552 A | | 8/1989 | Chaux |
| 4,973,300 A | | 11/1990 | Wright |

(List continued on next page.)

FOREIGN PATENT DOCUMENTS

| | | |
|---|---|---|
| EP | 0 487074 A1 | 5/1992 |
| FR | 1019217 | 1/1953 |
| FR | 2216893 | 2/1999 |
| WO | WO 95/15715 | 6/1995 |
| WO | WO 97/10753 | 3/1997 |
| WO | WO 98/27869 | 7/1998 |
| WO | WO 00/09017 | 2/2000 |
| WO | WO 00/42935 | 7/2000 |

OTHER PUBLICATIONS

Angelini, G.D., A Simple, Inexpensive Method of Heart Retraction During Coronary Artery Bypass Surgery, Ann. Thorac. Surg., vol. 46, pp. 246–247 (Aug. 1988).

Badellino, Michael M. Et Al., The Cardiac Rag, Simple Exposure of the Heart, Texas Heart Institute Journal, vol. 15, No. 2, pp. 134–135 (1988).

Gabbay–Frater Suture Guide, Triangulate, Track Suture Placement, Track Suture Placement in Valve, Seat Valve, Track Tied Sutures, Count needles; (Pages and Year Unknown).

Galvin, I.F. et al., Circumflex Exposure Using a Cardiac Sling; How to do it ; Ann. Thorac. Surg., vol. 49, pp. 833–834 (1990).

(List continued on next page.)

*Primary Examiner*—Gary Jackson
(74) *Attorney, Agent, or Firm*—Richard D. Allison; Thomas J. DesRosier (57) ABSTRACT

The present invention relates to suture organizing device for use with surgical retractors and devices for stabilizing a predetermined area of the body during a surgical procedure, more particularly to a suture organizing device that is attachable to surgical retractors used in connection with minimally invasive coronary artery bypass grafting surgical procedures and heart valve procedures, and more specifically to a suture organizing device having a plurality of suture slots thereon for the releasable attachment of sutures thereto during a surgical procedure to enable the surgeon to retract tissue from the surgical field and wherein the suture organizing device is oriented to extend laterally of the outer surface of the arms of the surgical retractor.

21 Claims, 7 Drawing Sheets

U.S. PATENT DOCUMENTS

| | | | |
|---|---|---|---|
| 5,167,223 A | | 12/1992 | Koros et al. |
| 5,207,703 A | | 5/1993 | Jain |
| 5,452,733 A | | 9/1995 | Sterman et al. |
| 5,509,890 A | | 4/1996 | Kazama |
| 5,613,937 A | | 3/1997 | Garrison et al. |
| 5,727,569 A | | 3/1998 | Benetti et al. |
| 5,728,151 A | * | 3/1998 | Garrison et al. ............... 623/2 |
| 5,749,892 A | | 5/1998 | Vierra et al. |
| 5,782,746 A | | 7/1998 | Wright |
| 5,836,311 A | | 11/1998 | Borst et al. |
| 5,875,782 A | | 3/1999 | Ferrari et al. |
| 5,894,843 A | | 4/1999 | Benetti et al. |
| 5,947,896 A | | 9/1999 | Sherts et al. |
| 5,957,835 A | | 9/1999 | Anderson et al. |
| 5,972,030 A | * | 10/1999 | Garrison et al. ........... 623/2.11 |
| 5,976,069 A | | 11/1999 | Navia et al. |
| 5,976,080 A | | 11/1999 | Farascioni |
| 6,010,531 A | * | 1/2000 | Donlon et al. ............... 623/2.1 |
| 6,015,427 A | | 1/2000 | Mueller et al. |
| 6,036,641 A | | 3/2000 | Taylor et al. |
| 6,102,853 A | | 8/2000 | Scirica et al. |

OTHER PUBLICATIONS

Kazama, Shigeru et al., Fabric Heart Retractor for Coronary Artery Bypass Operations, Ann. Thorac. Sug., vol. 55, pp. 1582–1583 (1993).

Matsuura, A. et al., Modified Janke Net Technique for Exposure of the Circumflex Artery, Thorac. Cardiovasc. Surgeon, vol. 40, pp. 158–159 (1992).

Matsuura, Akio et al., A New Device for Exposing the Circumflex Conronary Artery, Ann. Thorac. Surg., vol. 59, pp. 1249–1250 (1995).

Parsonnet, Victor et al., Self–Retaining Epicardial Retractor for Aortocoronary Bypass Surgery, Thoracic and Cardiovascular Surgery, pp. 629–630 ( Year Unknown).

Roux, D. et al., New Helper Instrument in Cardiac Surgery, Ann. Thorac. Surg., vol. 48, pp. 595–596 (1989).

\* cited by examiner

SUTURE ORGANIZING DEVICE FOR SURGICAL RETRACTOR AND METHODS RELATED THERETO

FIELD OF INVENTION

The present invention relates to a suture organizing device for use with surgical retractors and devices for stabilizing a predetermined area of the body during a surgical procedure, more particularly to a suture organizing device for use on a surgical retractor and devices used in connection with minimally invasive coronary artery bypass grafting surgical procedures or heart valve procedures.

BACKGROUND OF THE INVENTION

Diseases of the cardiovascular system affect millions of people each year and are a cause of death for large numbers of people in the United States and throughout the world. A particularly prevalent form of cardiovascular disease involves a reduction in the blood supply to the heart caused by atherosclerosis (coronary artery disease) or other conditions that create a restriction in blood flow at a critical point in the cardiovascular system leading to the heart.

One technique for treating such a blockage or restriction is a surgical procedure known as a coronary artery bypass graft procedure, which is more commonly known as "a heart bypass" operation. The surgical correction of occluded or stenosed coronary arteries by means of bypass grafting are probably still the most common procedures performed today, especially when multiple grafts are needed.

In the coronary artery bypass graft procedure, the surgeon either removes a portion of a vein from another part of the body for grafting or detaches one end of an artery and connects that end past the obstruction while leaving the other end attached to the arterial supply. When using a vein from another part of the body, the surgeon installs this portion at points that bypass the obstruction. In both cases, the objective is to restore normal blood flow to the heart.

In addition, when using this technique the surgeon makes a long incision down the middle of the chest, saws through the sternum, spreads the two halves of the sternum apart and then performs several procedures necessary to connect the surgical patient to a cardiopulmonary bypass machine to continue the circulation of oxygenated blood to the rest of the body while the heart is stopped and the graft is being sewn in place. Although such a procedure is one common technique for treatment, the procedure is lengthy, traumatic, expensive and can damage the heart, the central nervous system and the blood supply.

Interventional techniques, such as percutaneous transluminal angioplasty (PTCA) have gained popularity as the method of choice for therapy of atherosclerosis occlusions for several reasons. The transluminal approach is a less invasive technique that subjects the patient to reduced trauma and less recovery time, especially when compared to bypass grafts that utilize autologous tissue, such as saphenous vein grafts. Also, the patient often suffers complications at the donor site of the graft that may be worse than the sternotomy and anastomosis.

Although PTCA procedures are often successful, complications such as restenosis or thrombosis and embolism can occur. Restenosed vessels may also require surgical intervention for correction.

In recent years, and in an effort to reduce expense, risk and trauma to the patient, physicians have turned to less invasive and less traumatic surgical approaches to the heart. With such procedures, the heart is preferably beating during the surgical procedure. Thus, there is no need for any form of cardiopulmonary bypass and there is no need to perform the extensive surgical procedures necessary to connect the patient to such a bypass machine. Because these procedures are performed while the heart muscle is continuing to beat, the blood continues to flow and the heart continues to move in three dimensional movement while the surgeon is attempting to sew the graft in place. Also, the surgical procedure to install the graft requires placing a series of sutures through an extremely small vessel and onto tissue that continues to move during the procedure. It is necessary that these sutures be fully and securely placed so the graft is firmly in position and does not leak.

There is disclosed in U.S. Pat. No. 5,730,757, an access platform for the dissection of an internal mammary artery. The described access platform has first and second blades interconnected to a spreader member that laterally drives the blades apart together and support pads interconnected to the first blade. A torsional member is operably interconnected to the first blade and the spreader member and is used to vertically displace the first blade in either direction. Thus, increasing the surgeon's working space and visual access for the dissection of the internal mammary artery. A tissue retractor interconnected to the blades is used to draw the soft tissue around the incision away from the surgeon's work area. It is further provided that the access platform can include a port that can be used to mount a heart stabilizer instrument.

There also is described in U.S. Pat. No. 5,875,782 granted to Ferrari et al. and U.S. Pat. No. 5,894,843 granted to Benetti et al. an apparatus for stabilizing the predetermined area on a heart or other organ of a patient to enable a surgical procedure on a beating heart. The apparatus includes a bifurcated member having two elongated prongs and an elongated handle. The handle segment can be movably attached to a rib retractor so that a person is not required to hold the handle segment. In one disclosed embodiment, the apparatus further includes a device to hold the bifurcated member in a position against the surface of the heart sufficiently so that a stabilizing force is applied against the heart and contraction of the heart does not cause either vertical or horizontal motion at the target site during the surgical procedure.

There also is described in U.S. Pat. No. 5,836,311 granted to Borst et al. an apparatus for stabilizing the predetermined area on a heart or other organ of a patient to enable a surgical procedure on a beating heart. The apparatus includes a single legged or bifurcated member having a plurality of suction members thereon which are attached to the surface of the heart using suction pressure. The arm portion of this device can be movably attached to a rib retractor or other surgical device so a person is not required to hold the handle segment and the suction device may be locked into position against the surface of the heart.

In each of the above-described procedures, access to the heart tissue is an important consideration. Therefore, it is desirable to provide a suture organizing device to provide a quick and convenient way to organize and retain various sutures that are use to retain tissue such as pericardial tissue away from the operative field. Furthermore, during heart valve procedures, it is desirable to retain sutures in an organized manner to ensure that the proper sutures are tied together and that the sutures are not tangled during the valve sewing process and that all needles and sutures are accounted for at the end of the procedure.

U.S. Pat. No. 4,185,636 granted to Gabbay et al., discloses a commonly available suture organizer that is used in heart valve procedures to keep the sutures organized. This device includes a plurality of arcuate members that are attachable to the surgical drape. The arcuate members include slots therein to receive and retain the sutures therein as that the surgeon sews the heart valve in place. U.S. Pat. No. 4,492,229 granted to Grunwald discloses a device for attaching the "Gabbay-Frater" type of suture device to the top surface of a surgical retractor.

It desirable to provide a new system and devices related thereto for organizing sutures used in a coronary bypass procedure and in heart valve surgery and methods related thereto. With the recent advances in heart surgery procedures, it is important to provide systems that assist in reducing the time necessary to perform the surgery and to assist in keeping potential areas of confusion to a minimum. It is particularly desirable to provide such a system and devices thereto that are less complex and more user friendly in comparison to prior art devices. Furthermore, it is desirable to provide a system that is readily attachable to the existing devices so that it may be added and used during the procedure as needed by the surgeon. Such systems and devices thereto preferably are simple in construction, readily attachable to existing devices and less costly than prior art devices.

SUMMARY OF THE INVENTION

The present invention features a system for organizing sutures that are used for retracting, stabilizing, replacing or manipulating a predetermined area of a body. The system includes a suture organizing device that is readily usable with a surgical retractor and methods of use related thereto. The stabilization system and related devices and apparatuses thereto that are featured herein are described to illustrate a particularly preferred use of the present invention. Wherein the suture organizing device is advantageously used in performing off-pump coronary artery bypass grafting procedures in which the heart remains beating during the surgical procedure. One advantage of the present invention relates to the use of suture organizing device in combination with the external rail system on the arms of the retractor. The pericardium of the heart and other tissue retained away from the area of interest by passing the sutures through the pericardial tissue and then attaching the sutures to the suture organizing device to retain the sutures in a fixed and organized manner that does not affect the use of the surgical retractor or the stabilization system. The suture organizing device may be attached to the retractor prior to use or after the retractor has been used to open the chest of the patient. Additionally, the suture organizing device of the present invention may be sterilized and stored separately from the retractor so that it may be used or not used depending on the desires of the surgeon and the type of surgical procedure being performed.

In a general aspect of the present invention, the suture organizing device is preferably used for holding sutures that are attached to the pericardial tissue of a patient to ensure that the pericardial tissue does not interfere with the procedure. Alternately, the suture organizing device may be used in valve replacement procedures where numerous sutures are used to secure the new heart valve. The overall system described herein preferably also includes a retractor, a stabilization device for locally stabilizing the predetermined area and a stabilization arm that functionally secures the stabilization device to the retractor. The retractor preferably includes a rail system having two arms and a rack segment. The rack segment interconnects the two arms, for selectively spacing the two arms from each other and for maintaining the two arms in a desired fixed relationship. In a preferred form of the present invention, the two arms and rack segment are configured to receive the connector of the stabilization arm at the desired location thereon and the arms of the retractor are configured to receive the suture organizing device thereon. Additionally, it is anticipated that the suture organizing device may be further configured for releasable attachment to the rack segment of the retractor such as by adhesives or similar retention mechanisms.

The stabilization device preferably includes a device of the type commonly known as the Cohn Cardiac Stabilizer marketed by the Genzyme Corporation of Cambridge Mass., although horseshoe or suction type devices may also be used. The preferred form of the stabilization device is a generally square or rectangularly shaped member having a planar surface with centrally located opening therein. This opening is the area through which the surgeon performs the anastomosis or other procedure on the tissue of the beating heart. The stabilization device is preferably a two piece member so that once the anastomosis is completed, the pieces may be separated to remove the device from around the anastomosis. As described more fully below, flexible tapes are sutured through the tissue and then threaded through the stabilizing device. Once the stabilization device is positioned in the desired orientation and location in contact with the tissue, the flexible tapes are then pulled snug through the opening of the stabilization device to provide a system which minimizes the overall movement of the predetermined area of the tissue.

The stabilization arm preferably includes an elongated handle having a first end and a connector thereon for releasably connecting the stabilization device to the elongated handle first end. This connection allows the stabilization device to be pivotally and slidably moved to a desired position into contact with the predetermined area of the tissue of the patient. The stabilization arm also includes a mounting mechanism or sled member which is preferably slidable along the handle segment for removably securing the stabilization arm to at least one of the rails on the retractor arms and/or the rack segment of the retractor.

According to one aspect of the present invention, the arms of the retractor are configured with a front edge and a step in the top surface thereof to form an elongated rail surface along substantially the entire length thereof. The step is preferably spaced apart a predetermined and consistent distance from the front edge and is also located on the interconnecting or rack segment of the retractor. Also, the stabilization arm preferably includes a mounting mechanism or sled member which is configured to removably engage the front edge and the step at any desired location on one or more of the arms or the rack segment of the retractor. The mounting mechanism includes a lever for selectively engaging the step and front edge on the arm or rack segment of the retractor so the mounting mechanism is removably and slidably secured to the arms or the rack segment.

In another aspect of the preferred embodiment, there is featured a surgical retractor including two arms, a rack segment and a plurality of sternal blades with at least one blade extending downwardly from each arm. Each blade includes an upper section adjacent to the bottom surface of the arm and a lower section extending distally of the arm. A slot on the bottom surface of the arms includes a tapered surface adjacent to the front edge thereof to facilitate the placement of the blades on the arms. A lip surface is also located adjacent to the slots on the bottom surface of the arms to securely retain the blades on the bottom surface of the arms during the procedure while still allowing the blades to be easily removable for initial positioning and subsequent sterilization following the procedure. Furthermore, the suture organizing device of the present invention includes one or more connectors thereon that are configured to be received in the slots on the bottom surface of the arms. The suture organizing device is removably attached to the outer surface of the arms and includes a plurality of suture slots therein to securely receive sutures therein. The suture slots on the suture organizing device are preferably aligned with slots on the retractor to allow sutures to be placed therein so that the sutures do not interfere with the movement of the sled member along the arms or the adjustability of the stabilization system thereon.

In yet another aspect of the preferred embodiment, there is featured a sled member or mounting mechanism that allows the user to retain the stabilization arm in a sliding and fixed relationship relative to the retractor and patient while also allowing for the rotation of the sled member with respect to the retractor by manipulating a single knob. Furthermore, a lever on a bottom section of the sled member allows the sled member to be slidably and fixedly positioned along the arms and rack segment of the retractor. Each of these features enables the user to determine the optimum position for the stabilization arm and stabilization device while ensuring that the surgeon's view of the operative area is not unnecessarily obstructed. Additionally, these features allow the present invention to be used in many different medical procedures because of the versatility of system set up and orientation of the components of this invention.

Other aspects and embodiments of the invention are more fully discussed below.

BRIEF DESCRIPTION OF THE DRAWINGS

For a fuller understanding of the nature and desired objects of the present invention, reference is made to the following detailed description taken in conjunction with the accompanying drawing figures wherein like reference numbers denote corresponding parts throughout the several views and wherein.

DESCRIPTION OF THE PREFERRED EMBODIMENT

Referring now to the various figures of the drawings wherein like reference characters refer to like elements, there is shown various views of a preferred and alternate form of a suture organizing device 200 for use with a stabilization system 100 according to the present invention for organizing sutures used in a medical procedure. The stabilization system 100 is particularly useful in connection with single or multiple vessel off-pump coronary artery bypass surgery on a beating heart through a sternotomy or mini-sternotomy incision.

A surgeon may use the stabilization system 100 to apply a slight contacting or compressive force on the heart in the area where the surgical procedure will occur so the heart's movement at that specific area is diminished. In a preferred form of this device, the stabilization system 100 is used in combination with flexible tapes or sutures or other mechanical means so that the surface of the heart is stabilized using a combination of restraining and stabilizing forces. In certain procedures, it may also be advantageous to place a traction suture around an artery using a needle and suture thread to occlude the blood vessel. These sutures may then be attached to the stabilizing device so that the flow of blood through the blood vessel is selectively restricted.

The suture organizing device 200 of the present invention is particularly useful for various techniques or procedures on the heart of a patient where it is desirable to organize multiple sutures. Another area of use of the present invention may be in brain surgery, heart valve surgery or other types of blood vessel surgery where accuracy and speed is critically important to avoid disastrous consequences or where it is desirable to have a precisely defined and readily viewable surgical field. One skilled in the art will appreciate that the present invention, although advantageously suited for heart surgery, can be used at any location on or within the body where multiple sutures are used and access to tissue or isolation of a predetermined area is desired. This includes, but is not limited to, the liver, kidneys, bladder, stomach, intestines, brain and vascular and other soft tissue surgery.

Referring specifically to FIGS. 1, 2, 3A and 3B, the stabilization system 100 according to the present invention includes a retractor 102, a stabilization sub-system or stabilization arm 104 and a stabilization device 106. The retractor 102 is specifically configured so the stabilization arm 104 can be secured thereto. The retractor 102, preferably includes a rigid L-shaped member 110 having an arm segment 112 and a rack segment 114. The retractor 102 also includes a movable second arm segment 116 having a handle 118 thereon which is movably associated with the L-shaped member 110.

The stabilization arm or sub-system 104 preferably includes an elongate arm segment 180 that preferably interconnects the retractor 102 and the stabilization device 106. The arm segment 180 preferably includes a first end having a distal connector 181 thereon to pivotally and removably retain the stabilization device 106 thereon. The arm segment 180 is attachable to the retractor 102 by a connector such as a mounting mechanism or sled member 140. The proximal or second end of the arm segment 180 preferably includes a knob 184 thereon that is rotatable with respect to the arm segment 180 to allow the movement of the stabilization device 106 to be pivotal and/or fixed with respect to the arm segment 180 by manipulating the knob 184 on the proximal end of the arm segment 180. This arrangement also allows the stabilization device 106 to be mountable on and removable from the distal connector 181.

The preferred form of the stabilization device 106 is generally a rectangular shape having an opening or window area 190 therein. The stabilization device 106 preferably includes a first surface 192 that is generally planar and may include a textured surface thereon to facilitate the engagement between the stabilization device and the tissue of the predetermined area or the heart of the patient. The second surface 194 of the stabilization device 106 preferably includes a post member extending therefrom. The post member is preferably releasably and rotatably engaged by the distal connector 181 on the first end of the arm segment 180.

As described briefly above, the retractor 102 preferably includes a handle 118 located on the second arm segment 116 and the handle 118 is rotatable for displacing the two arm segments 112, 116 with respect to each other. Rotation of the handle 118 preferably causes a pair of posts or pinions 119 to sequentially engage the teeth 115 located on the outer edge 121B of the rack segment 114 to increase or decrease the distance between the first and second arms 112 and 116. As shown, the handle includes a projection 177 on the bottom surface thereof that fits in a slot located in the retractor adjacent to the arm and rack segment to allow the user to lock the handle into position once the arms are in the desired position. This feature is particularly useful where the retractor is used for a relatively long period of time for multiple procedures because the pinions and teeth on the retractor will gradually wear due to the pressure from the chest of the patient. As the wear occurs, the pressure from the sternum may cause the arms to move towards each other unless the arms or handle are retained in a locked position. In a specific illustrative embodiment, the rack segment 114 is configured with a finochetti type of rack as is known to those skilled in the art. In conjunction with the handle 118, the rack segment 114 and movable second arm 116 form a rack and pinion type of means for displacing the arm segments 112, 116 with respect to each other. As shown, this type of rack segment 114 includes a plurality of laterally extending teeth members 115 that engage the posts 119 or similar tooth engaging members located in operative contact with the handle 118 of the second arm segment 116. It is anticipated that a variety of mechanisms may be used to move the second arm segment 116 along the rack segment 114. For example, a gear mechanism, a slide and locking mechanism or similar arrangement may be used to accomplish the separation and fixation of the second arm 116 with respect to the first arm 112.

At least one arm segment and preferably each arm segment, 112 and 116 respectively, and the rack segment 114 are configured so as to each have a front edge surface 120A, 120B and 120C extending along the inner surface of each element of the retractor 102 such that the front edges of each of the arms and the rack segment face each other. The retractor 102 also preferably includes an outer edge surface 121A, 121B and 121C extending along the outer surface of the first and second arms, 112 and 116 respectively, of the retractor 102. A step surface 122A, 122B and 122C extends along the top surface of the first and second arms, 112 and 116 respectively, and the rack segment 114 in a spaced apart relationship with respect to the front edges of each of the surfaces of the first and second arms and the rack segment to form an elongate lip or external rail surface on the arms and rack segment of the retractor. The step surface 122A–C is preferably located a preset distance back from the front edge and forms an acute angle facing away from the front edge thereof on each of the arms and the rack segment. As described hereinafter, the front edge surfaces 120A–C and the step surfaces 122A–C on the top surface of the arms and rack segment are particularly arranged and configured to face each other and so that the mounting mechanism or sled member 140 can be readily secured to the retractor 102 by engaging the front edge surface (120A, 120B or 120C) and the associated step surface (122A, 122B or 122C) on each of the first and second arms, 112 and 116, and the rack segment 114.

Figure 1:
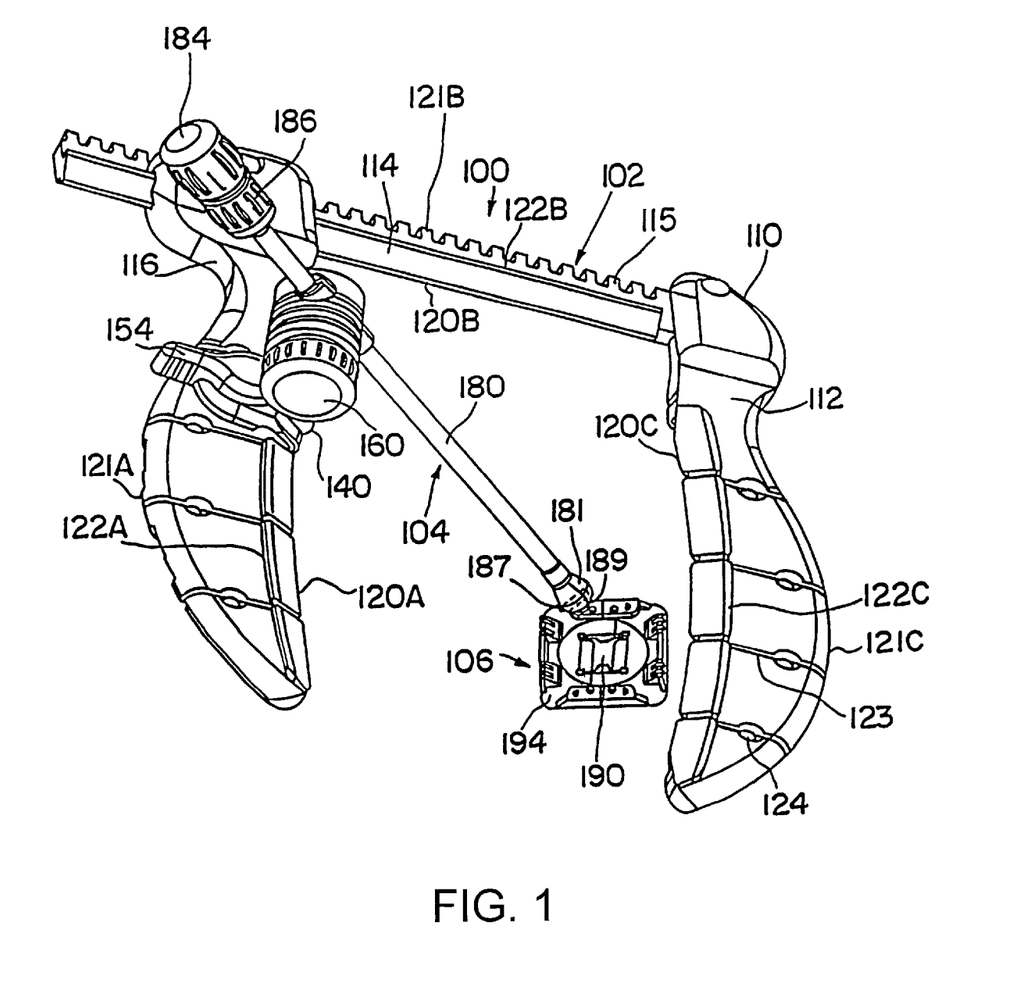
FIG. 1 is a perspective view of a stabilization system that assists in the stabilization of a predetermined area of a body according to a first aspect of the present invention with the handle removed for clarity.
Figure 2:
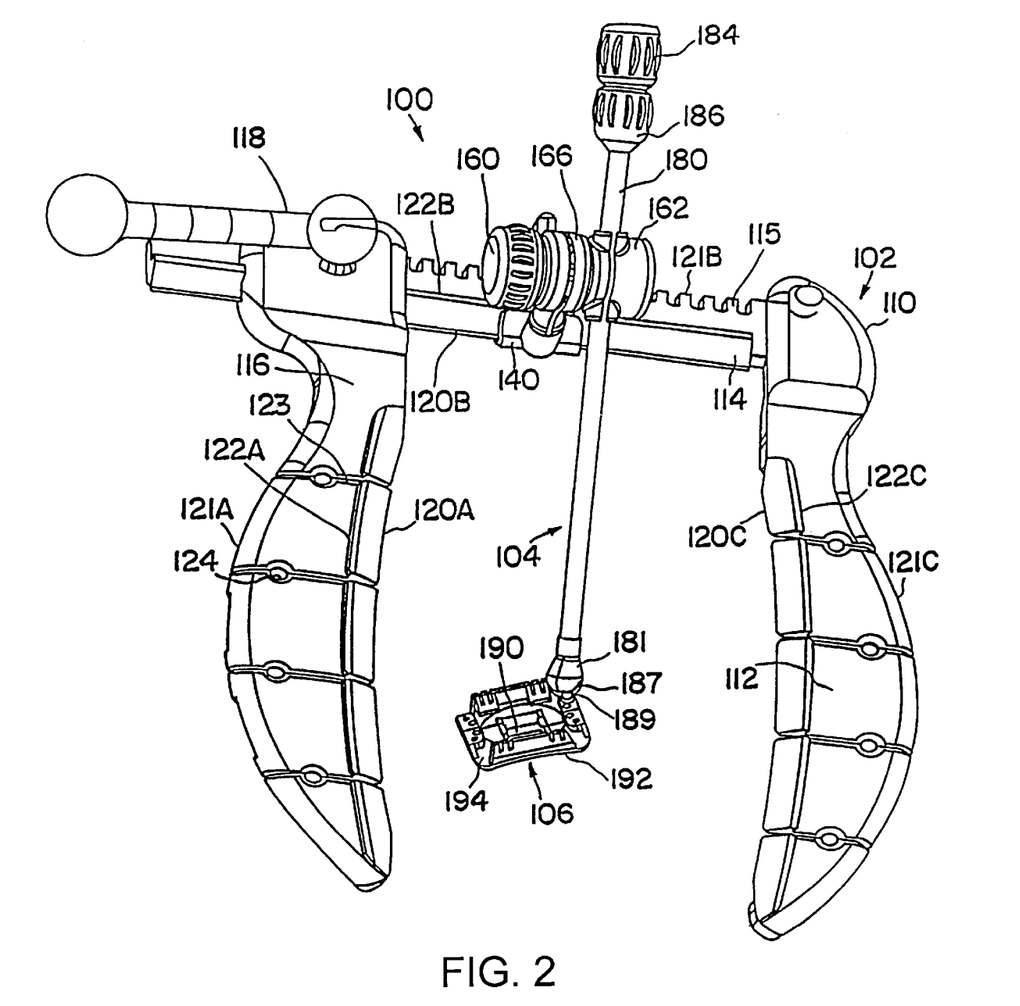
FIG. 2 is a perspective view of the stabilization system of the present invention and wherein the sled member is positioned on a rack segment of the retractor.

As also shown in the top views of the preferred form of the present invention, the front edge surfaces 120A and 120C of the first and second arm segments that are adjacent to the step surfaces 122A and 122C are of a preferably slightly concave orientation such that the mid point of the first and second arms are spaced apart from each other a greater distance than the distance of either or both of the inner or outer ends of the first and second arms, 112 and 116. Additionally, the outer edge surfaces 121A and 121C of each arm preferably has a greater curvature than the front edge surfaces 120A and 120C of the same arm so that as the retractor 102 spreads the chest of the patient, the motion of separating the first and second arms, 112 and 116, is emphasized to increase the amount the chest of the patient is spread. Therefore, at a given distance of separation between the first and second arms, 112 and 116, the midpoints of the outer surface of the arms will be separated a further distance than at the ends adjacent to the rack segment or at the ends furthest from the rack segment 114 due to the overall generally clam shell shaped configuration of the preferred form of the present invention. An advantage of this configuration is that the surgeon is provided with an opening in the sternum of the patient that is wider in the center than along the edges so that the most common area of work for the surgeon is larger than a conventional retractor for the same amount of separation.

Additionally, as shown in the drawings, the top surface of each of the arms, 112 and 116, preferably include a plurality of slots 123 extending generally perpendicular to the lengthwise dimension of each arm. These slots 123 extend from the front edge surfaces 120A and 120C; through the step surfaces 122A and 122C; and to the outer edge surfaces 121A and 121C, respectively on each of the first and second arms, 112 and 116. These slots 123 are configured to extend through the front edge surface 120A and 120C of each arm, 112 and 116, to allow the sled member 140 to be moved therealong while not cutting or interfering with any sutures that may be positioned in the slots. Additionally, each of the slots 123 preferably include a through hole 124 in communication with the slot and extending through the arm. In the preferred use of the present invention, the slots 123 are used to position sutures that have been threaded through the pericardium of the patient therethrough so that the pericardium or other tissue is retracted and held out of the line of sight of the surgeon by the sutures to better expose the heart of the patient. With the preferred form of the present invention, the sutures may be retained out of the working area of the surgeon by clamping the end of the suture to the surgical drape while passing the suture through the slots 123 and retaining the suture below the top surface of the retractor.

Figure 3A:
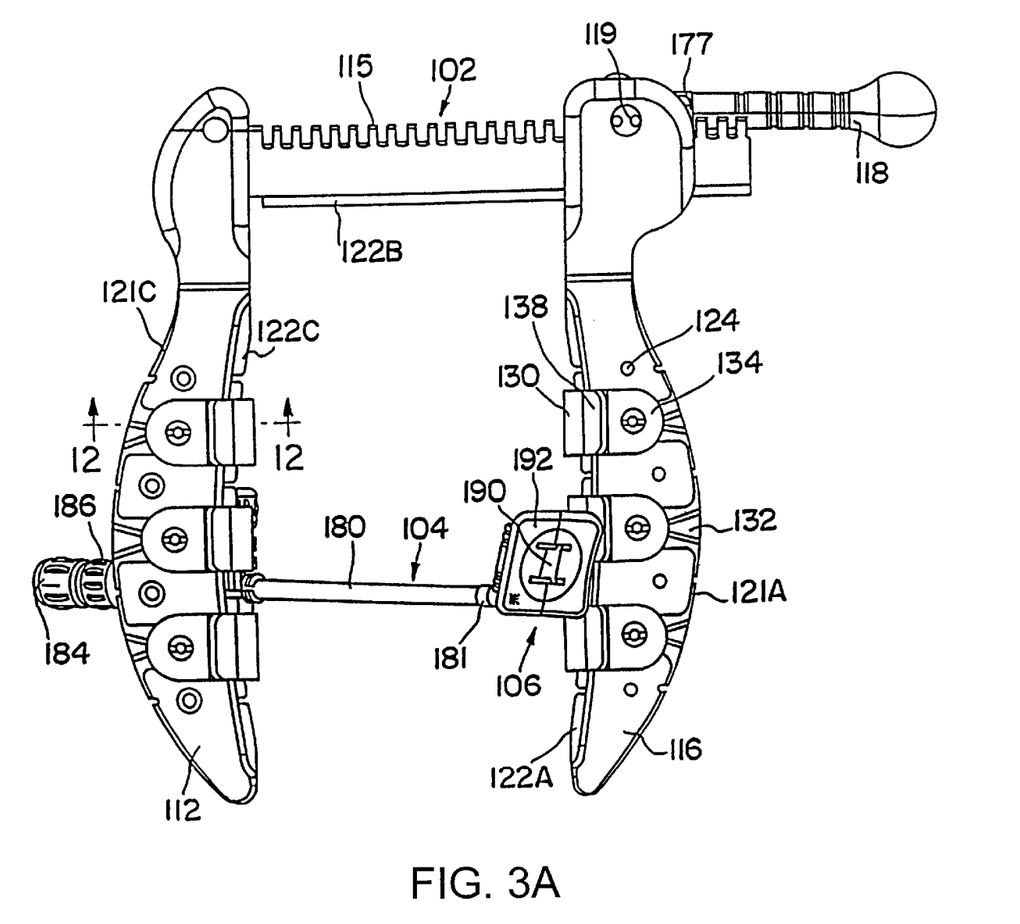
FIGS. 3A and 3B are bottom perspective views showing the stabilization system of the present invention.
Figure 3B:
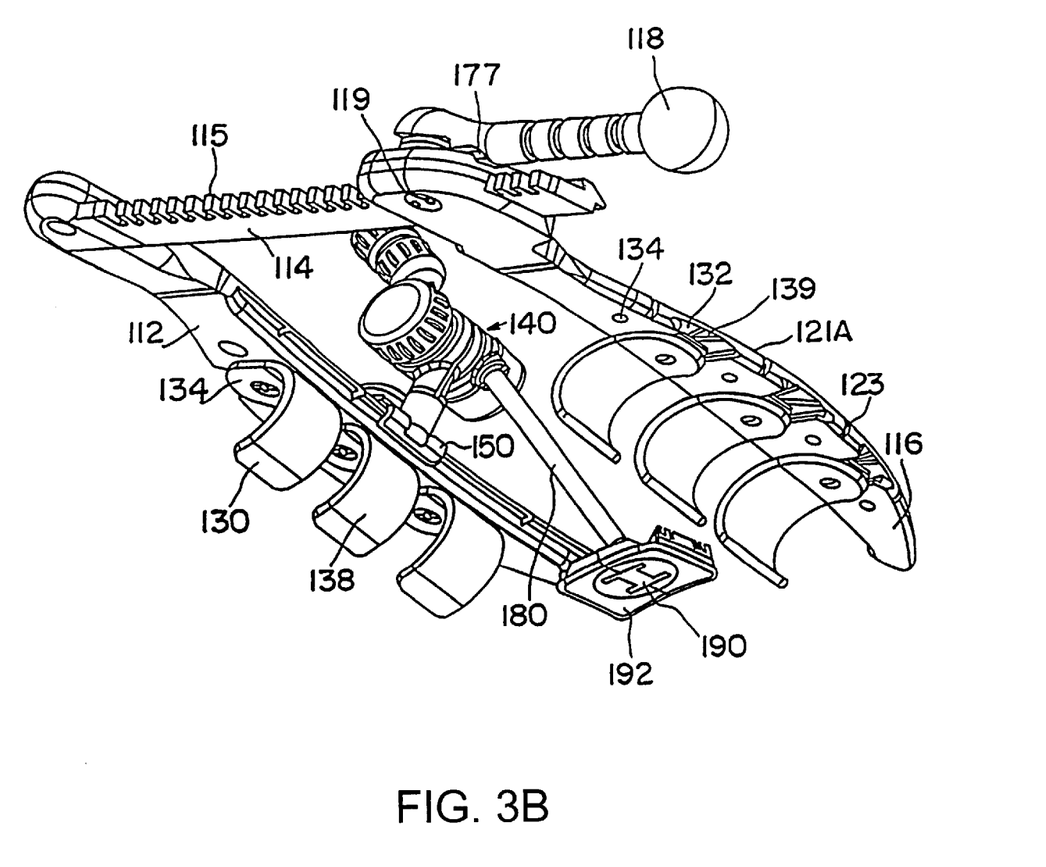

In an exemplary embodiment of the present invention, the bottom surface of each of the first and second arms, 112 and 116, on the retractor 102 include removable sternal blades 130 attached thereto. Each blade 130 is removable so as to facilitate the use of the retractor in a full or mini-sternotomy procedure by allowing for the selective positioning and spacing of the blades 130 as desired for the particular procedure as well as for resterilization of the retractor 102 and blades 130. As illustrated, the blades 130 are positioned along the bottom surface of the arms 112 and 116 and are preferably pivotal in the horizontal and vertical directions with respect to the arms. The blades 130 are slidable into elongate ridged slots 132 on the bottom surface of the first and second arms, 112 and 116. The blades 130 may swivel a limited distance and are selectively positioned in the slots 132 so as to evenly distribute the retraction forces or pressure along the contour of the sternum of the patient. An upper section 134 of each blade 130 is particularly configured to facilitate the insertion of the blades into the retractor. As the arms are retracted, the inner and outermost blades move to a retraction position to assume a slightly curved shape. In the preferred form of the present invention, the retraction position generally approximates the anatomy of the patient and allows the pressure of the sternum of the patient to be evenly distributed among the blades.

The stabilization sub-system or stabilization arm 104 of the present invention preferably includes an elongate arm segment 180 that interacts with the retractor 102 and the stabilization device 106. The arm segment 180 is preferably a rigid tubular member that includes a distal connector 181 on the distal end thereof to pivotally and removably retain the stabilization device 106 thereon. The arm segment 180 is attachable to the retractor 102 by a connector such as a mounting mechanism or sled member 140. The proximal end of the arm segment 180 preferably includes a movable knob 184 and a fixed knob 186 thereon. The movable knob 184 is connected to an elongate rod that is threaded through the arm segment 180 and extends to the distal connector 181. The fixed knob 186 is fixed proximally of the movable knob 184 on the arm segment 180 to allow the user to rotate the stabilization device 106 by manipulating this fixed knob 186 when the stabilization device 106 is connected to the distal connector 181 of the arm segment 180.

As illustrated, the distal connector 181 consists of a generally bulbous member having an elongate slot 187 extending through at least one side thereof. The slot 187 is sized to allow the post member of the stabilization device 106 to pass laterally therethrough to allow the stabilization device to be easily mounted on or removed from the stabilization arm 104. Additionally, the shape of the post member and the complementary shape of the slot 187 allows the stabilization device to be pivotal and rotatable about the handle segment to enable the surgeon to position the stabilization device 106 in the desired position and against nearly any surface of the heart of the patient. The stabilization device 106 is fixed in the desired position relative to the arm segment 180 by rotating the movable knob 184 with respect to the handle segment and/or the fixed knob so that a portion of the elongate rod moves with respect to the outer surface of the arm segment 180 and extends into the distal connector 181 to contact and engage the post member of the stabilization device 104. This movement of the elongate rod with respect to the distal connector causes the post member to press against the lower lip surfaces 189 of the distal connector. The preferred, generally pear-like, shape of the distal connector 181 optimizes the connection between the distal connector 181 and the post member to enable the stabilization device 106 to be selectively retained within the distal connector 181 while allowing for the pivotal and rotational movement necessary for the use of this device in a cardiac application where space is at a premium and the device must be as versatile as possible to accommodate the surgeons needs without undue experimentation.

Figure 4:
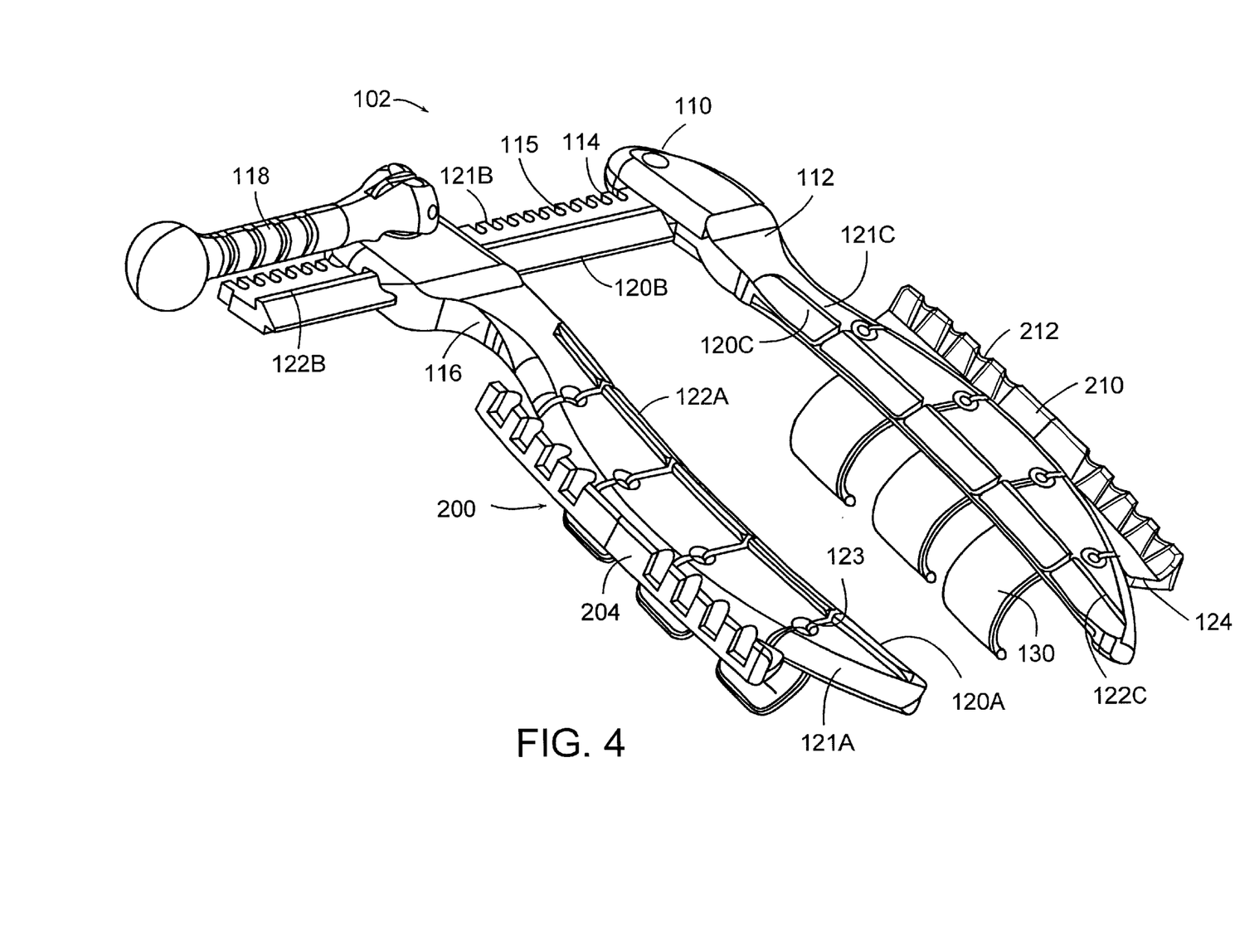
FIG. 4 is a perspective view showing the suture organizing device attached to the surgical retractor of FIG. 1 with the stabilization system removed for clarity.
Figure 5:
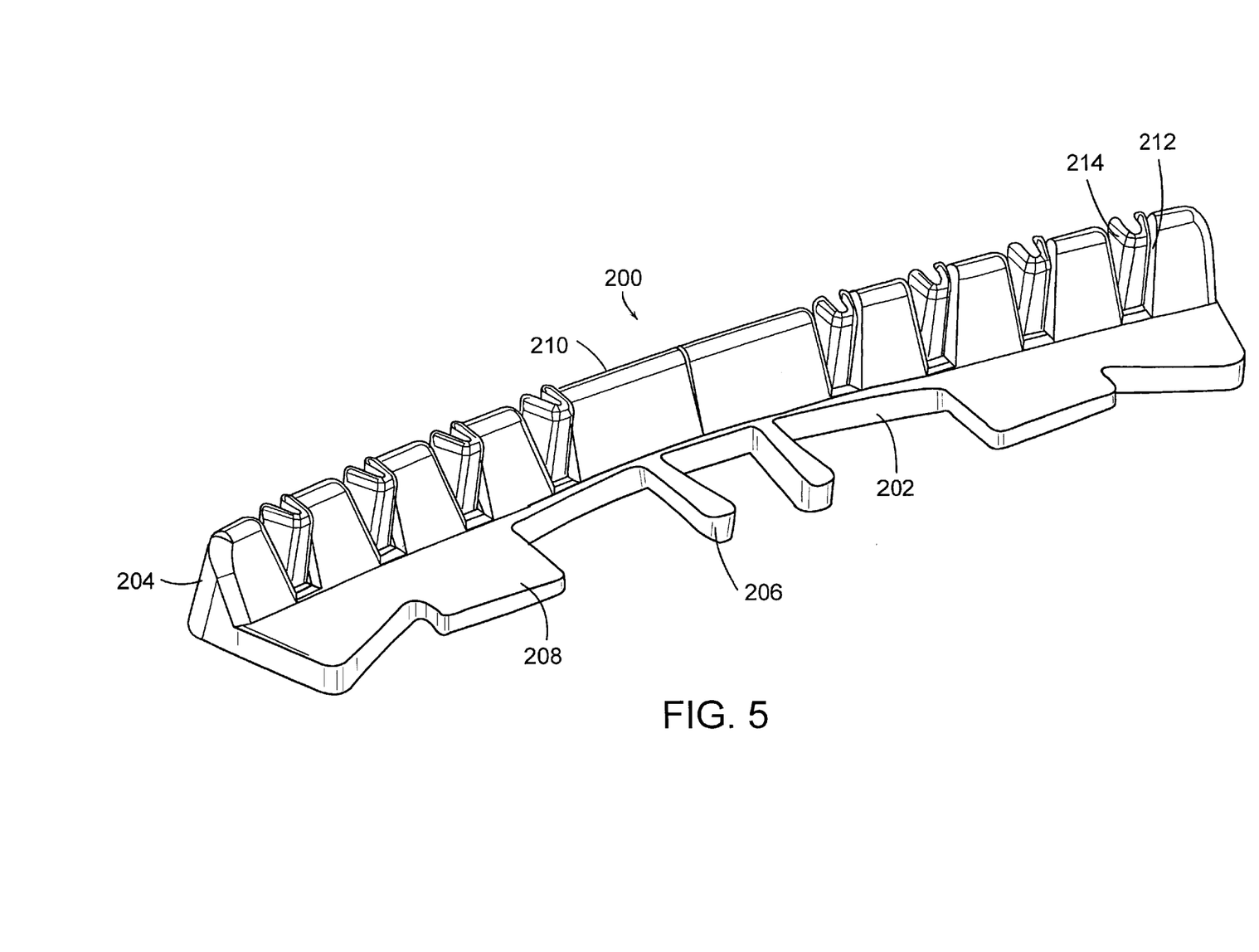
FIG. 5 is an enlarged view of the suture organizing device of FIG. 4.

The stabilization arm 104 of the preferred embodiment also includes a sled member 140 operatively connected thereto. The sled member 140 is configured so the surgeon has multiple axis positioning capability for the stabilization device 106 while requiring a minimum of manipulation. In the preferred embodiment, the sled member 140 provides the surgeon with the rotational movement of the stabilization arm 104 in a combination of horizontal and vertical directions as well as allowing for the sliding and rotational movement of the arm segment 180 therethrough, all of which are advantageously controlled by the operation of the single knob 160 that is located along the periphery of the operative field The use of the stabilization system 100 described herein can be used in combination with the suture organizing device 200 shown in the drawings and described herein. The suture organizing device 200 is preferably attachable to the outer surface of the arms 112 and 116 of the retractor 102 to generally laterally extend therefrom. The suture organizing device preferably includes an inner surface 202 and an outer surface 204 and has an overall slightly arcuate configuration. The inner surface 202 preferably includes a pair of clip members 206 that are sized and configured to extend inwardly therefrom and be releasably received in one of the elongate ridged slots 132 on the bottom surface of the first and second arms, 112 and 116 of the retractor 102. Additionally, the inner surface 202 of the suture organizing device 200 also preferably includes a plurality of lip members 208 which are longitudinally spaced apart from the clip members 206 and extend inwardly from the inner surface 202 to assist in stabilizing the suture organizing device 200 with respect to the arms of the retractor 102. The lip members 208 are configured to fit within or adjacent to the pair of elongate ridged slots 132 located adjacent to the slot 132 that receives the clip members 206 therein. The remaining portion of the inner surface 202 of the suture organizing device 200 is preferably slightly arcuate to conform to and abut against the outer surface of the retractor 102.

The suture organizing device 200 also preferably includes an upper surface 210 that is generally adjacent to and is positioned along the outer surface 204 of the retractor 102. As shown, the upper surface includes a series of spaced apart suture slots 212. In a preferred form of the present invention, the suture slots are arranged in groups of equally spaced apart suture slots such that the slots 123 on the retractor are provided with adjacent pairs of slots 212 on the suture organizing device 200 such that each suture that is placed in the slot 123, may be placed in at least two suture slots 212. As shown, the embodiment illustrated in the drawings includes four slots 123 on each arm of the retractor and preferably about eight suture slots 212 on the suture organizing device to enable the surgeon to select the desired slot and suture slots to retain the suture. The suture slots 212 consist of generally V-shaped slots that are sized to releasably receive a suture therein. In use, the suture is pulled down into the slot and the gradually decreasing width of the slot functions to releasably retain the suture therein. Alternately, the suture slots 212 may include a flexible retention member 214 therein. The retention member 214 is preferably compressed in the suture slots and functions to frictionally retain the sutures therein. In the preferred form of the present invention, the suture slots 212 are arranged in spaced apart pairs or groups of suture slots 212 to provide the surgeon with multiple attachment points for the suture. Additionally, as shown, at least one suture slot 212 of each group of suture slots 212 is aligned with each slot 123 on the adjacent arms 112 and 116 of the retractor 102. In the more preferred form of the present invention, at least two of the suture slots 212 are aligned with each slot 123 on the retractor. This arrangement enables the surgeon to place a suture, such as the suture holding the pericardium of the patient, through the slot 123 on the retractor and into the suture slots 212 on the suture organizing device 200. This generally linear alignment between the slot 123 and the suture slot 212 allows the suture to be positioned beneath the upper surface of the arms of the retractor so that the suture does not interfere with the movement of the sled member along the retractor and so that the suture is not accidentally cut during use or movement of the stabilization system. Additionally, multiple sutures may be positioned in the slot 123 on the retractor and then attached to the same or different suture slots 212 in a manner desired by the surgeon.

Figure 6:
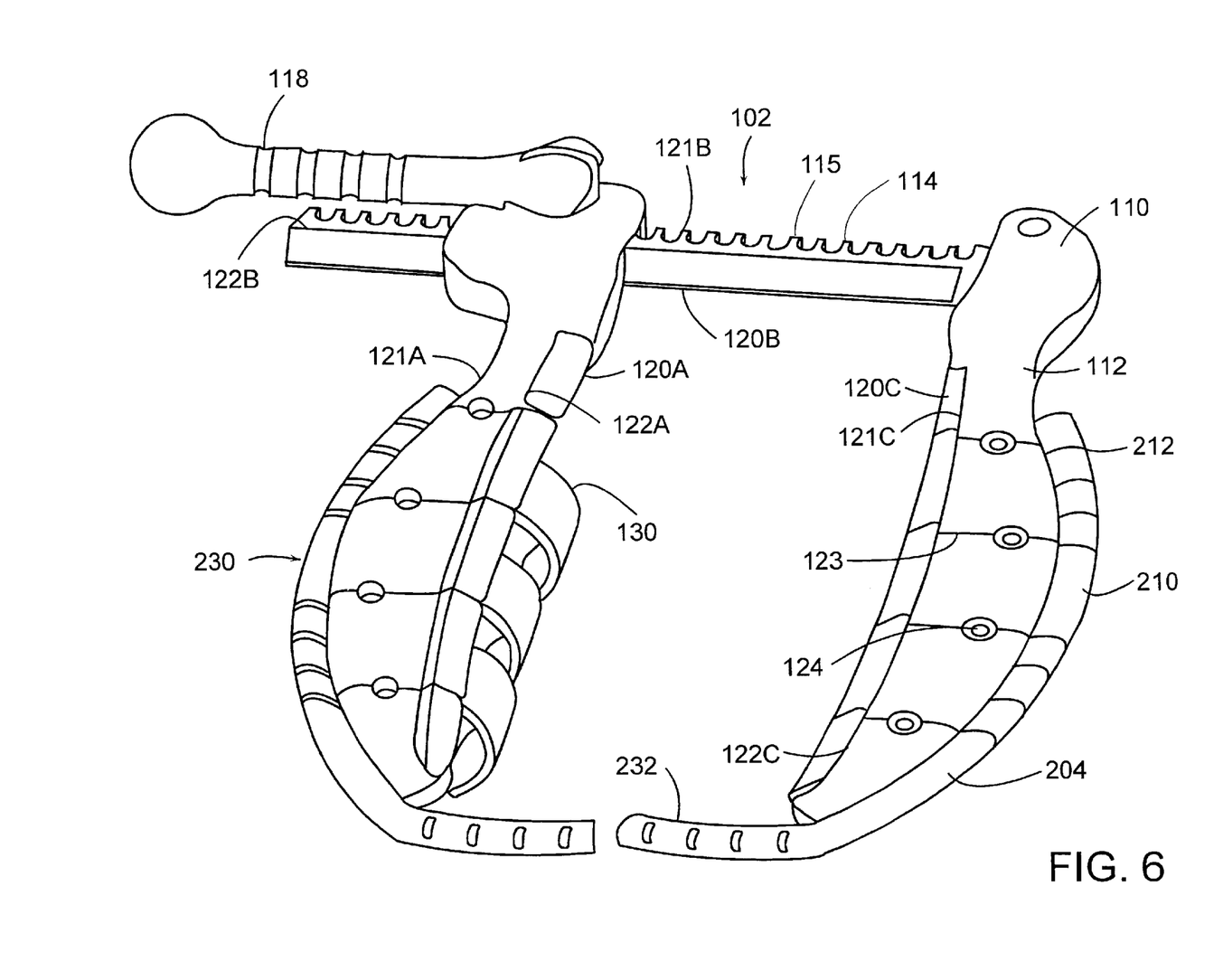
FIG. 6 is a perspective view of an alternate form of the suture organizing device of the present invention attached to the surgical retractor of FIG. 1 with the stabilization system removed for clarity.

FIG. 6 is illustrative of a further embodiment of the present invention. In this embodiment, the suture organizing device 230, includes a pair of extensions 232 thereon in addition to the suture slots 212 described above. These extensions 232 extend inwardly of the arms 112 and 116 of the retractor 102 to form further suture attachment locations for the surgeon. This arrangement is particularly useful when the surgical procedure requires the use of several sutures to retain the pericardium of the patient in a non-interfering position as well as to further position additional portions of tissue, such as the wall of the heart. Additionally, this arrangement is also particularly useful in heart valve procedures because more sutures are used and it is extremely important that the sutures are retained in an organized manner. This embodiment of the present invention is very versatile and may be used for nearly any heart procedure where it is desirable to retain tissue out of the surgical field and/or organize numerous sutures. For example, there are certain commercially available pads or slings to assist in the positioning of the heart of the patient to provide access to the blood vessels on the side or back of the heart. It may be desirable to use the suture organizing device to retain this type of device in the desired position. Additionally, whenever the surgeon performs a surgical procedure on the wall or valves of the heart, it is desirable to ensure that the sutures and needles are retained in an organized manner on the suture organizing device 200.

In this embodiment, the extensions 232 are aligned generally parallel to the rack segment 114 of the retractor 102 and are generally perpendicular to the lengthwise dimension of the arms 112 and 116 of the retractor. Additionally, one or two extensions 232 may be used and the suture organizing device 230 may be attached to the retractor 102 either prior to use or following the use of the retractor 102 to open the chest of the patient. As shown, the extensions 232 preferably include additional suture slots 212 that are spaced apart from the suture slots that are located adjacent to the arms of the retractor. It is anticipated that the used of the extensions will provide the surgeon with the ability to temporarily retain sutures in the extensions 232 during the procedure and also retain the sutures in an additional plane and location that is separate from the arms of the retractor. For example, this may be particularly useful in various valve procedures where the surgeon desires to temporarily retain numerous sutures along the periphery of the valve.

The method of using the suture organizing device of the present invention is believed to be best understood from the following discussion with reference to the drawings. As described briefly above, the retractor 102 preferably includes a handle 118 located on the second arm segment 116 and the handle 118 is rotatable for displacing the two arm segments 112, 116 with respect to each other. Although the following discussion makes reference to the use of the stabilization system specifically in connection with a coronary artery bypass grafting surgical procedure, the use of the present invention is not limited to such uses.

After appropriately preparing and positioning the patient for the surgical procedure and completing those actions required in advance of the use of the stabilization system, the arms 112 and 116 of the retractor 102 would be closed such that the upper portion 134 of the blades 130 are generally abutting each other and the suture organizing device may be attached to the retractor. The surgeon then positions the lower sections 138 of each of the blades adjacent to the incision and pushes down on the retractor or otherwise manipulates the blades and the patient so the blades are pushed through the incision and past the sternum.

After inserting the retractor, the surgeon displaces the two retractor arm segments 112, 116 with respect to each other by rotating the handle 118 on the second arm segment 116. As the surgeon opens the sternum of the patient, they also release any underlying connective tissue and open the pericardium surrounding the heart of the patient. In order to provide for visualization of the heart, the pericardium that surrounds the heart is retracted by placing sutures (not shown) through the pericardium and then threading the sutures through the slots 123 on the retractor arms and into the suture slots 212 on the suture organizing device 200 to ensure that the sutures are spaced apart from the operative field and securely retained in the desired position. This allows the sutures to be positioned out of the way of the surgeon for the subsequent procedure and eliminates the prior use of various clamps being used to on the surgical drape to hold the sutures. After performing any subsequent actions to further open the sternum of the patient to create the desired field of view and assess the viability of the heart to perform the bypass grafting procedure on one or more vessels, the surgeon mounts the stabilization arm 104 onto one of the retractor arm segments 112, 116 or the rack segment 114 in the position that they anticipate will provide the best access while minimizing the obstruction of their view for the particular procedure.

It should be recognized that the bypass grafting procedure may involve the coronary arteries or branches thereof on nearly any surface of the heart including the posterior or backside of the heart. Therefore, having the capability to mount the stabilization arm to the rack segment 114 or either of the arms, 112 or 116, of the retractor can be particularly advantageous. With the preferred form of the present invention, the stabilization arm 104 may be positioned near the top of the operative field on the rack segment 114 rather than only along the sides of the operative field. The retractor 102 is typically arranged on the body so the throat of the retractor faces the head of the patient and the surgeon is typically located on one side of the patient while a nurse is located on the other side of the patient and instruments are passed across the body of the patient throughout the procedure. Therefore, with the preferred form of the present invention, the surgeon has an additional surface to choose from when they are deciding which surface will provide the best access to the desired surface of the heart while not interfering with the procedure. Additionally, with the alternate embodiment of the present invention, the surgeon will also have an additional location to position the retention sutures to further ensure that they have adequate access and visualization of the desired surgical field.

To mount the stabilization arm 104 onto the retractor 102, the surgeon rotates the sled actuator lever 154 so the second lip is in a disengaged position and is spaced from the front edge lip 150 of the sled member 140. After so configuring the sled member 140, the surgeon positions the sled member 140 on the retractor 102 at any of a number of available positions on the arms, 112 and 116, or the rack segment 114 by positioning the front edge lip 150 over the front edge of the selected arm or rack segment. With the preferred configuration of the sled member 140, the surgeon need not slide the sled member along the entire length of a retractor arm or be required to select from a limited number of predetermined positions, but can place the sled member 140 directly at the desired position. In this way, a surgeon can removably position the sled member 140 anywhere on the rack segment 114 or the arms 112, 116 of the retractor 102 without having to first assemble the retractor with a sled member 140 initially positioned in any of these predefined areas. An advantage of this configuration is that the surgeon may initially position the sled member 140 in a position that they anticipate will be close to where they will ultimately want it. If a different location is needed or provides better access, the surgeon may move the actuator lever 154 and either slide the sled member 140 along the previously selected arm or rack segment to the desired location or they may remove the sled member 140 from the retractor and try various locations to see which location on the arms and rack segment provides the best access for the particular procedure. In addition, such a sled configuration also allows the surgeon to perform certain surgical procedures without having to worry about the sled member 140 cutting or interfering with any sutures that may be passing through the slots in the retractor while positioning the sled member 140. This configuration also ensures that the surgeon will not have to reposition any of the previously positioned retention sutures because it is necessary to adjust the sled member or any other component on the retractor. Furthermore, if multiple blood vessels are operated on or access to multiple surfaces is desired, the orientation of the sled member may be readily adjusted to accommodate the needs of the particular part of the procedure.

Once the surgeon is satisfied with the location of the stabilization device 106 on the heart of the patient, the surgeon may tighten knobs 160 and 184 to ensure that the stabilization arm 104 and stabilization device 106 are retained in the desired position throughout the remainder of the procedure. Once the stabilization device 106 is in the desired contacting relationship with the predetermined area of the heart, the surgeon may tighten the knob 160 of the stabilization arm 140 so as to prevent further rotation about the threaded rod and the sled pin and also to prevent sliding of the handle segment in the aperture. The surgeon may also tighten the knob 184 of the arm segment 180 so as to tighten the connection between the distal connector 181 on the handle segment and the post member on the stabilization device 106 prevent further motion of the stabilization device 106 about the end of the stabilization arm 104.

After completing the grafting procedure, the surgeon may then remove the stabilization arm 104 and stabilization device 106 by essentially reversing the above described steps or the surgeon may simply release the actuator lever 154 and remove the entire stabilization arm and stabilization device from the operative field. Similarly, the actuator lever may be moved to a position between the engaged and disengaged positions so that the stabilization arm may be moved out of the way while a subsequent procedure is performed or to attach a new stabilization device thereon. Additionally, the retention sutures may be released from the suture organizing device and the tissue returned to the desired position. If sutured needles have been used, they may be returned to the scrub nurse for counting as they are released or they may be temporarily reattached to the suture organizing device for later counting and tracking.

In the foregoing discussion, the suture organizing device of the present invention is described in terms of being used in combination with a stabilization system for clamping and supporting a stabilization device. It is within the scope of the present invention, however, for the system to be configured to removably secure sutures, ligatures or similar medical devices used in any of a number of surgical procedures.

Although a preferred embodiment of the invention has been described using specific terms, such description is for illustrative purposes only, and it is to be understood that changes and variations may be made without departing from the spirit or scope of the following claims.

What is claimed is:

1. A system for use in a surgical procedure, comprising:
   a retractor having a plurality of retractor arms thereon and a segment interconnecting said retractor arms wherein said retractor arms are movable with respect to each other;
   a medical device operatively positionable with respect to said retractor and said medical device being movable relative to the retractor to a desired position during a medical procedure; and
   a suture organizing device which is selectively mountable on each of said retractor arms of said retractor.

2. The system of claim 1 wherein said retractor arms include inner and outer surfaces and said suture organizing device is mountable along said outer surface of said retractor arms.

3. The system of claim 2 wherein each of said retractor arms have a top surface and at least one slot extending laterally therealong and said suture organizing device includes at least one suture slot aligned therewith.

4. The system of claim 1 wherein said suture organizing device includes width and lengthwise dimensions and a top surface with an elongate and upwardly projecting member along the lengthwise dimension of at least a portion thereof and said projecting member includes a plurality of suture slots extending along the width dimension of the projecting member.

5. The system of claim 4 wherein said projecting member is an elongate rail extending substantially parallel to at least one of said plurality of retractor arms and said suture organizing device is removably attachable thereto.

6. The system of claim 1 wherein said retractor arms include inner and outer surfaces and said suture organizing device includes a connector thereon to releasably engage a portion of at least one of said retractor arms so that said suture organizing device extends laterally from said outer surface of at least one of said retractor arms.

7. The system of claim 6 wherein said suture organizing device includes suture slots therein and said suture slots are sized to releasably receive sutures therein.

8. The system of claim 7 wherein said suture slots are organized into a plurality of groups of suture slots on said suture organizing device.

9. The system of claim 1 wherein said retractor arms include inner and outer surfaces and at least one elongate slot extending therebetween and said suture organizing device is aligned generally along said outer surface of at least one of said retractor arms said suture organizing device includes a projecting member extending generally lengthwise along said suture organizing device and said projecting member is aligned with said outer surface of said at least one of said retractor arms and includes at least one suture slot thereon that is generally aligned with said slot on said at least one retractor arm.

10. A suture organizing system for use in a surgical procedure, comprising:
   an elongate suture organizing device having a length dimension, a width dimension and a top surface wherein suture organizing device is formed as a semicircular member and includes an inwardly directed connector thereon that is sized for attachment to a surgical retractor and the top surface of the suture organizing device includes an upwardly projecting member extending along the lengthwise dimension thereof and said projecting member includes a plurality of suture slots extending through a portion thereof.

11. The system of claim 10 wherein said suture slots are oriented generally parallel to the width dimension of the suture organizing device and said slots are sized to releasably retain a suture therein.

12. The system of claim 10 wherein said suture organizing device includes a second member thereon that extends inwardly of said projecting member and said second member further includes suture slots thereon.

13. The system of claim 10 wherein said suture organizing device includes a base section having said connector thereon and said base member is sized so that at least a portion thereof is in contacting engagement with a surgical retractor in use.

14. A suture organizing system for use in a surgical procedure, comprising:
  an elongate suture organizing device having a length dimension, a width dimension and a top surface wherein suture organizing device includes a connector thereon that is sized for attachment to a surgical retractor and the top surface of the suture organizing device includes an upwardly projecting member extending along the lengthwise dimension thereof and said projecting member includes a plurality of suture slots extending through a portion thereof;
  wherein said suture organizing device includes a second member thereon that extends inwardly of said projecting member and said second member further includes suture slots thereon; and
  wherein said second member is oriented generally perpendicular to said projecting member.

15. A suture organizing system for use in a surgical procedure, comprising:
  an elongate suture organizing device having a length dimension, a width dimension and a top surface wherein suture organizing device includes a connector thereon that is sized for attachment to a surgical retractor and the top surface of the suture organizing device includes an upwardly projecting member extending along the lengthwise dimension thereof and said projecting member includes a plurality of suture slots extending through a portion thereof;
  wherein said suture organizing device includes a second member thereon that extends inwardly of said projecting member and said second member further includes suture slots thereon; and
  wherein said suture slots of said projecting member are oriented generally perpendicular to said suture slots of said second member.

16. A suture organizing system for use in a surgical procedure, comprising:
  an elongate suture organizing device having a length dimension, a width dimension and a top surface wherein suture organizing device includes a connector thereon that is sized for attachment to a surgical retractor and the top surface of the suture organizing device includes an upwardly projecting member extending along the lengthwise dimension thereof and said projecting member includes a plurality of suture slots extending through a portion thereof;
  wherein said suture organizing device includes a base section having said connector thereon and said base member is sized so that at least a portion thereof is in contacting engagement with a surgical retractor in use; and
  wherein said projecting member is generally aligned with said base section and said base section is located on an inner surface of said suture organizing device and said projecting member is located on an outer surface of said suture organizing device.

17. The system of claim 16 wherein said suture slots are aligned with the width dimension of said suture organizing device on said projecting member and said suture slots are spaced apart from said base section.

18. The system of claim 17 wherein said suture slots are arranged in distinct groups of suture slots along said projecting member.

19. The system of claim 17 wherein said suture slots are arranged on said projecting member such that at least one suture slot is aligned with a slot located on an arm of a surgical retractor when said connector is in engagement with the suture retractor.

20. A suture organizing system for use in a surgical procedure, comprising:
  an elongate suture organizing device having a length dimension, a width dimension and a top surface wherein suture organizing device includes a connector thereon that is sized for attachment to a surgical retractor and the top surface of the suture organizing device includes an upwardly projecting member extending along the lengthwise dimension thereof and said projecting member includes a plurality of suture slots that are oriented generally parallel to the width dimension of the suture organizing device and said slots are sized to releasably retain a suture therein extending through a portion thereof; and
  a base section having said connector thereon and said base member is sized so that at least a portion thereof is in contacting engagement with a surgical retractor in use and wherein said projecting member is generally aligned with said base section and said base section is located on an inner surface of said suture organizing device and said projecting member is located on an outer surface of said suture organizing device.

21. The system of claim 20 wherein said suture organizing device includes a second member thereon that extends inwardly of said projecting member and said base section said second member further includes suture slots thereon and said suture slots of said projecting member are oriented generally perpendicular to said suture slots of said second member.

* * * * *